(12) United States Patent
Strube et al.

(10) Patent No.: US 7,615,159 B2
(45) Date of Patent: Nov. 10, 2009

(54) METHOD FOR THE PRODUCTION OF CHEMICAL AND PHARMACEUTICAL PRODUCTS WITH INTEGRATED MULTICOLUMN CHROMATOGRAPHY

(75) Inventors: Jochen Strube, Hagen (DE); Karsten-Ulrich Klatt, Leverkusen (DE); Gerhard Noeth, Köln (DE); Joern Greifenberg, Bergisch Gladbach (DE); Sebastian Böcker, Leverkusen (DE); Heinz Kansy, Köln (DE); Peter Jähn, Leverkusen (DE); Berthold Justen, Burscheid (DE)

(73) Assignee: Bayer Technology Services GmbH, Leverkusen (DE)

( * ) Notice: Subject to any disclaimer, the term of this patent is extended or adjusted under 35 U.S.C. 154(b) by 61 days.

(21) Appl. No.: 11/569,473

(22) PCT Filed: May 14, 2005

(86) PCT No.: PCT/EP2005/005313

§ 371 (c)(1),
(2), (4) Date: Oct. 18, 2007

(87) PCT Pub. No.: WO2005/113101

PCT Pub. Date: Dec. 1, 2005

(65) Prior Publication Data

US 2008/0135483 A1 Jun. 12, 2008

(30) Foreign Application Priority Data

May 21, 2004 (DE) .................. 10 2004 025 000

(51) Int. Cl.
*B01D 15/08* (2006.01)
(52) U.S. Cl. ................... 210/659; 210/198.2

(58) Field of Classification Search .................. 210/635, 210/656, 659, 662, 198.2; 127/46.1, 46.2
See application file for complete search history.

(56) References Cited

U.S. PATENT DOCUMENTS

| 3,268,605 | A | | 8/1966 | Boyd, Jr. |
| 3,706,612 | A | | 12/1972 | Palmer |
| 4,434,051 | A | | 2/1984 | Golem |
| 4,499,115 | A | | 2/1985 | Minh et al. |
| 5,126,055 | A | | 6/1992 | Yamashita et al. |
| 5,434,298 | A | | 7/1995 | Negawa et al. |
| 5,565,104 | A | * | 10/1996 | Priegnitz ..................... 210/659 |
| 5,578,215 | A | | 11/1996 | Hotier et al. |
| 5,578,216 | A | | 11/1996 | Hotier et al. |

(Continued)

FOREIGN PATENT DOCUMENTS

DE 19833502 2/1999

(Continued)

OTHER PUBLICATIONS

Journal of Chromatography, 590 (1992), pp. 113-117.

*Primary Examiner*—Ernest G Therkorn
(74) *Attorney, Agent, or Firm*—Norris McLaughlin & Marcus, P.A.

(57) ABSTRACT

The invention relates to a chromatographic process for substance separation in the context of the preparation of chemicals such as, for example, chiral pharmaceuticals, isomers or biomolecules on the small-scale and production scale, based on Simulated Moving Bed (SMB=countercurrent chromatography) technology.

7 Claims, 9 Drawing Sheets

U.S. PATENT DOCUMENTS

| | | | |
|---|---|---|---|
| 5,582,736 A | 12/1996 | Hotier et al. | |
| 5,635,072 A * | 6/1997 | Moran | 210/659 |
| 5,685,992 A | 11/1997 | Cohen et al. | |
| 5,762,806 A | 6/1998 | Hotier | |
| 6,063,285 A | 5/2000 | Hotier et al. | |
| 6,096,218 A | 8/2000 | Hauck et al. | |
| 6,136,198 A | 10/2000 | Adam et al. | |
| 6,217,774 B1 * | 4/2001 | Nagamatsu et al. | 210/659 |
| 6,500,342 B1 * | 12/2002 | Ogawa et al. | 210/659 |
| 7,544,293 B2 * | 6/2009 | Oroskar et al. | 210/198.2 |

FOREIGN PATENT DOCUMENTS

| | | |
|---|---|---|
| EP | 0688588 | 12/1995 |
| EP | 0688589 | 12/1995 |
| EP | 0688590 | 12/1995 |
| EP | 0688690 | 12/1995 |
| EP | 0960642 | 12/1999 |
| WO | WO 91/13046 | 9/1991 |
| WO | WO 92/16274 | 2/1992 |
| WO | WO 93/04022 | 3/1993 |
| WO | WO 00/25885 | 5/2000 |

* cited by examiner

Figure 3 Timing 1 of the SMB cycle
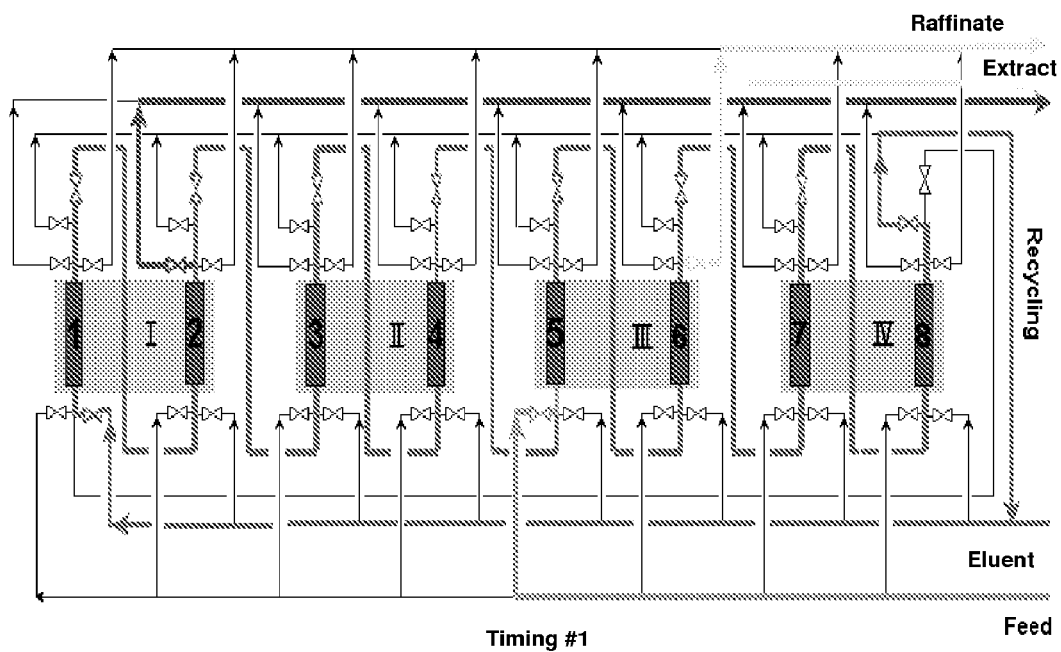

Figure 4 Timing 2 of the SMB cycle
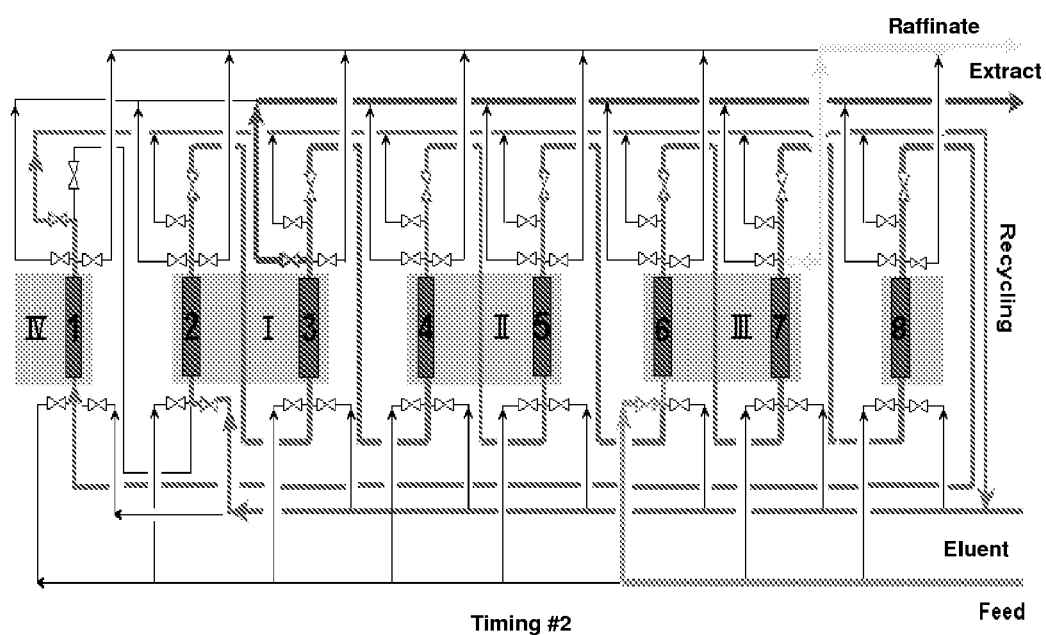

Figure 5: Example of a racemate separation:
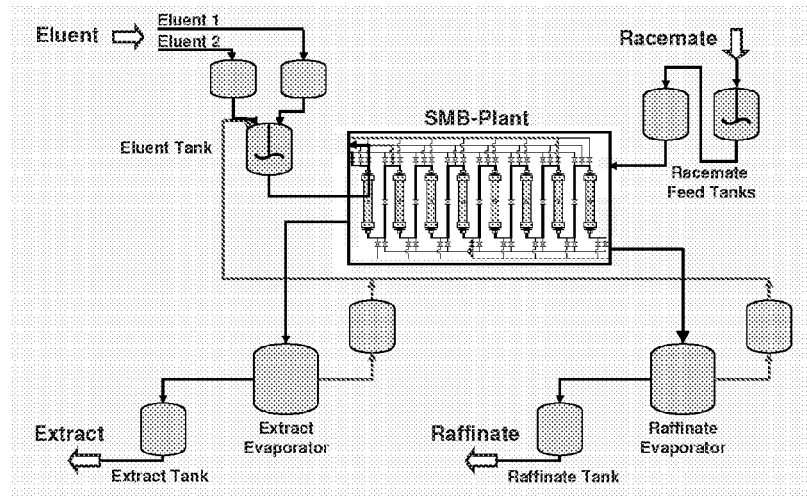
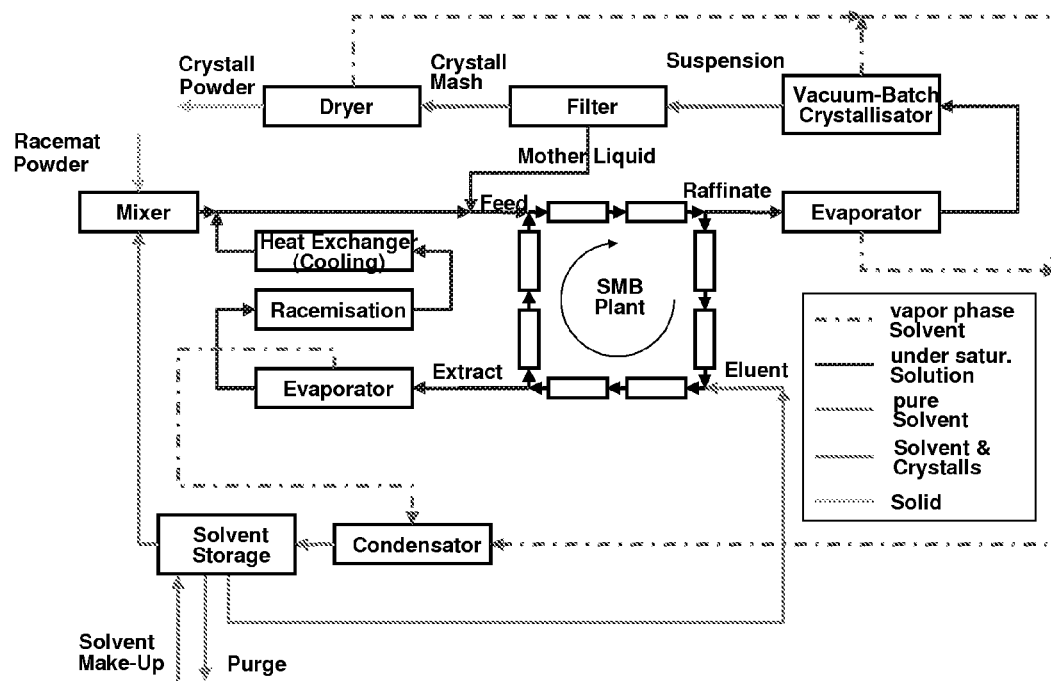

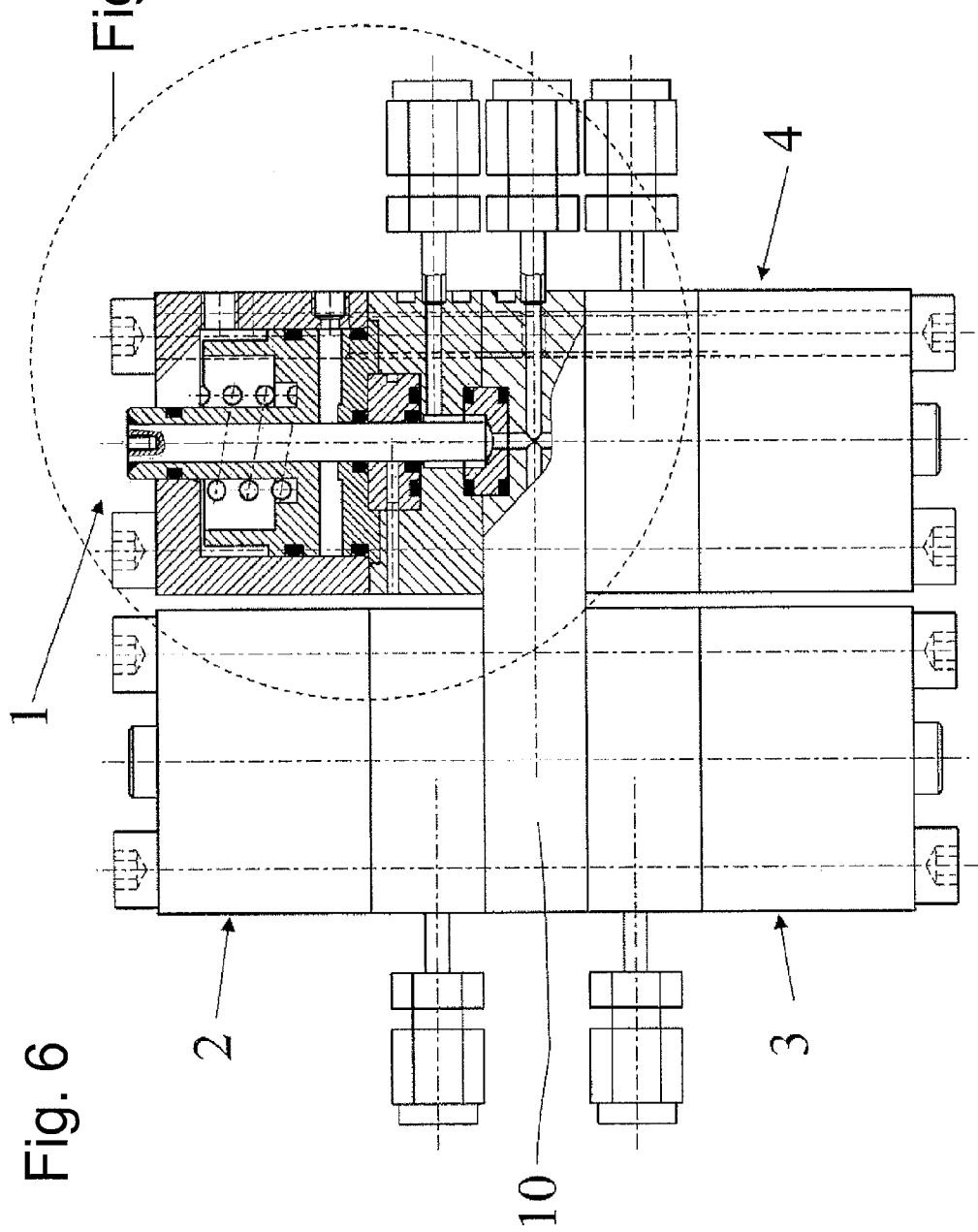

METHOD FOR THE PRODUCTION OF CHEMICAL AND PHARMACEUTICAL PRODUCTS WITH INTEGRATED MULTICOLUMN CHROMATOGRAPHY

REFERENCE TO RELATED APPLICATIONS

This application is a 371 of PCT/EP2005/005313 filed May 14, 2005.

The invention relates to a chromatographic process for substance separation in the context of the preparation of chemicals such as, for example, chiral pharmaceuticals, isomers or biomolecules on the small scale and production scale, based on Simulated Moving Bed (SMB=countercurrent chromatography) technology.

SMB is a process which allows continuous substance separations by imitating (simulating) the countercurrent between the adsorbent and mobile phase (liquid, gas or in the supercritical state).

U.S. Pat. No. 3,706,612 of A. J. de Rosset and R. W. Neuzil describes a simulated moving bed (countercurrent chromatography) unit on the pilot scale. Likewise, an operating problem is described there when such units are operated on the large scale and a circulating pump is utilized in order to guarantee the circulation of the liquid in the process. This invention (U.S. Pat. No. 3,706,612) describes the use of a valve at the starting end of each adsorber bed in order to prevent an opposed flow.

U.S. Pat. No. 4,434,051 of M. W. Golem describes an apparatus which allows countercurrent chromatography by utilizing a large number of multiway valves instead of a single rotary valve.

The separation of racemic mixtures on chiral adsorbents is described in an article in the Journal of Chromatography, 590 (1992), pp. 113-117; an alternative arrangement of 8 adsorption chambers and 4 rotary valves is utilized there.

U.S. Pat. No. 3,268,605 describes a control system which controls the flow rate of three of the main streams by flow regulators and the fourth stream by means of a pressure regulator. A similar control concept for chiral substance systems is described in WO 92/16274 of Bayer AG. This reference uses a number of two-way valves in order to simulate the countercurrent of the adsorbent.

In all these known techniques, however, the separating capacity is impaired by the holdup volume of the circulation flow pump, which must be compensated by additional measures, such as, for example, asynchronous timing, alteration of the column lengths or flow adjustment [such as, for example, in EP 0688590 A1, Sepharex (Novasep), "Totvolumenkompensation der Kreislaufpumpe durch Reduktion des Volumens" (Dead volume compensation of the circulating pump by reduction of the volume) (Länge); "asynchronous timing" as in EP 0688589 A1, Sepharex (Novasep); EP 0688588 A1 "Durchsatzänderung der Rezyklierpumpe" (Throughput alteration of the recycling pump)]. In DE 19833502 A1 of Novasep, for this, the SMB base regulation by means of pressure is described by simultaneous variation of at least two throughputs.

Consequently, the asynchronous timing in one zone was further developed to asynchronous timing in a number of or all zones (WO 00/25885 A).

For example, WO 93/04022 A of Daicel in which SMB is employed for resolution with subsequent re-racemization of the unwanted isomer, or WO 91/13046 A of Daicel which likewise describes the use of SMB with a chiral stationary phase for resolution afford examples of the use of SMB technology.

The prior art for the regulation of the internal and external mass flows in simulated countercurrent chromatography is described, for example, in U.S. Pat. Nos. 4,499,115, 5,685, 992, 5,762,806, EP 960642 A1 and DE 19833502 A1.

Customarily, for the transport of the fluids 5 pumps are employed there, in each case one pump being located in the corresponding supply and outlet lines—feed, eluent, extract and raffinate lines, and a further pump is arranged within a closed circuit. For the simulation of the solid countercurrent, after a specific time interval, the timing period $\tau$, is retimed, i.e. by means of appropriate valve circuits the addition and removal sites are displaced around a column in the flow direction of the fluid phase. The circulating pump thus "migrates" through the individual zones and transports different volume flows during a cycle.

FIG. 2 shows a customary SMB process. The fluid stream flows on SMB operation in the circulation of a number of fixed bed columns filled with adsorbent. The unit is subdivided into four functional zones by the continuous addition or removal of the feed, desorbent, extract and raffinate streams. Each one of these zones here takes on a special separation or workup function. Also shown is the recycle stream, transported by a recycle pump. Each functional zone, between the positions of the external supply and discharge streams, are in each case situated one to a number of chromatographic columns. The concentration profile established on suitable choice of the operating parameters in the cyclically stationary state within the SMB unit of the main components to be separated is shown schematically in the right section of FIG. 2 relative to the positions of the supply and discharge streams at the point of time of the end of the cycle.

FIGS. 3 and 4 show schematically the apparatus construction of a customary SMB process with the arrangement of individual valves in two successive cycles. In the supply line of each column 2 individual valves for the switching of alternative feed or eluent stream and in the outlet line of each column 3 individual valves for alternative raffinate, extract or recycling stream. On each further cycle, the valve circuits are displaced by one position to the next column.

If the connecting lines between the columns are of different length and contain a dead volume not to be neglected compared to the column volume, this fact must be taken into account, and a worsening of the separating capacity possibly associated therewith must be counteracted. Asynchronous switching of the valves (EP 688589 B1), specific adjustment of the zone volumes (EP 688690 B2) or an adjustment of the output of the circulating pump (EP 688588 B1) provide possible corrective measures.

For continuous operation as intended, the most exact possible adherence to the internal and external mass flows is an indispensable requirement. For this, customarily three of the four supplied and discharged mass flows ($Q_F$, $Q_D$, $Q_{Ex}$ and $Q_{Raf}$) are constantly controlled, while the fourth part of the flow is readjusted by means of a specified system pressure such that this system pressure remains constant, by which the overall mass balance is adhered to.

This so far customary mode of operation of SMB chromatography units therefore has the following serious disadvantages:

The pressure regulation must on the one hand compensate all malfunctions in the area of the mass flows as quickly and exactly as possible, on the other hand it is itself in some cases perceptibly disturbed by operation-related pressure variations (e.g. also by the cyclical switching processes). In particular in the case of high purity requirements and/or short cycle times, this can lead to instabilities up to the loss of the separating capacity.

The locking of the mass balance by means of pressure regulation requires a permanently closed circulation. Short-term opening of the circulation, e.g. for the discharge of impurities is thereby not possible.

The internal circulating pump is confronted with continuously changing mass flows, in addition this type of switching causes variable dead volumes and thus inherent process malfunctions, which must be compensated. As already mentioned, this frequently proves to be difficult, in particular in the case of short cycle times and demanding separation tasks.

In circuit operation as intended, in the SMB process generally 4 internal ($Q_I$, $Q_{II}$, $Q_{III}$ and $Q_{IV}$) and 4 external mass flows ($Q_F$, $Q_D$, $Q_{Ex}$ and $Q_{Raf}$) exist, which are linked to one another by means of the following mass balances $$Q_I = Q_D + Q_{IV}$$

$$Q_{II} = Q_I - Q_{Ex}$$

$$Q_{III} = Q_{II} + Q_F$$

$$Q_{IV} = Q_{III} - Q_{Raf} \quad (1)$$

For the setting of the working point, 3 external and one internal mass flow and the timing period $\tau$ must be specified in such a way that the separating task is achieved and thereby economical optimum operation is obtained with adherence to the specified product purities. The timing period $\tau$ here determines the "speed" of the apparent solid countercurrent.

In the entire prior art, for the operation of the SMB, however, circulation pumps are fundamentally employed, which leads to the problems already described due to the holdup volume of the pump.

It has now surprisingly been found that contrary to expectation no circulation flow pump is necessary in order to maintain the fluid circulation in an SMB.

BRIEF DESCRIPTION OF THE DRAWINGS

FIGS. 3 and 4 show schematically the apparatus construction of a customary SMB process with the arrangement of individual valves in two successive cycles.

FIG. 5 shows the integration of the multicolumn chromatography process in an overall process for the preparation of chemical and pharmaceutical substances as exemplified by racemic substances.

FIG. 6 shows a four-valve block with master board.

DESCRIPTION OF THE PREFERRED EMBODIMENTS

The present invention therefore relates to an SMB process in which instead of the previously customary 5 pump concept a 4 pump concept is used by pumping the eluent stream with constant flow and extract, raffinate and feed stream. For the two outlet streams, alternatively control valves instead of forced delivery pumps are also possible here.

Figure 1:
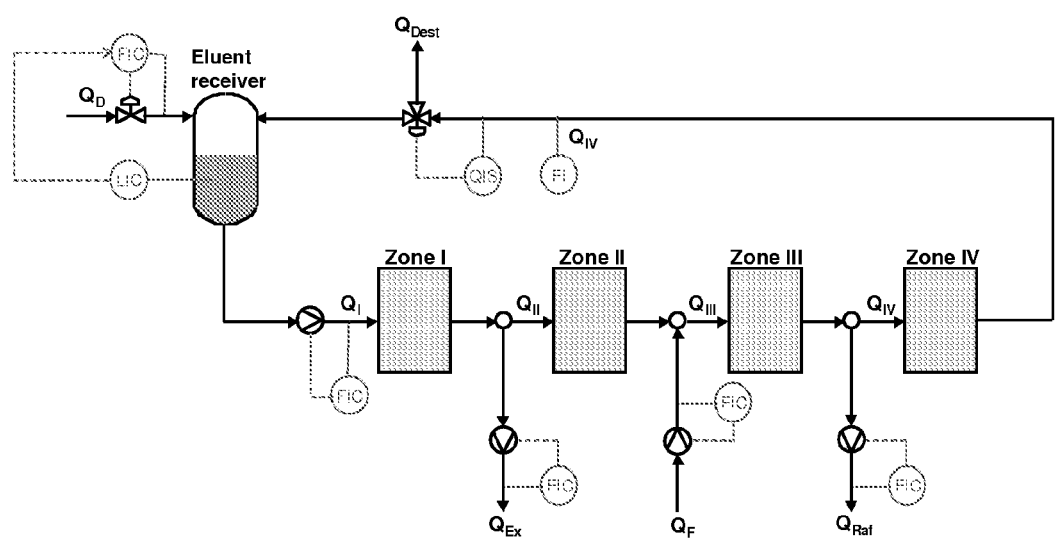
FIG. 1 shows the principle of the SMB chromatography unit according to the invention.
Figure 2:
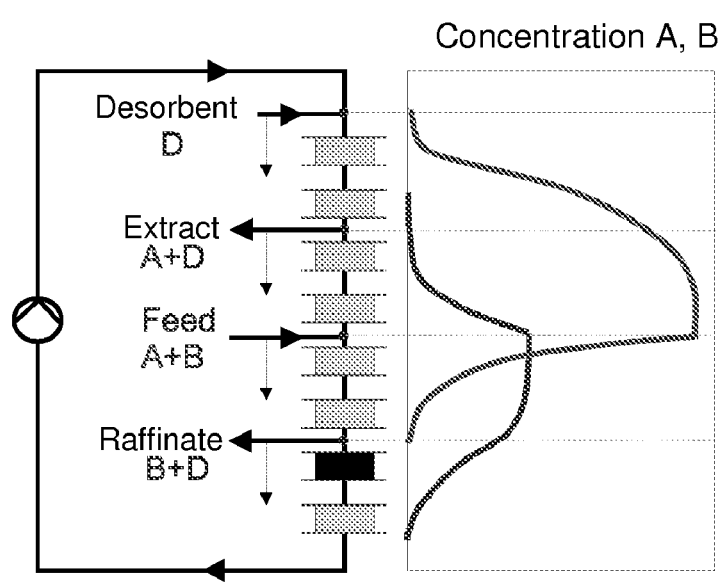
FIG. 2 shows a customary SMB process.

FIG. 1 shows the principle of the SMB chromatography unit according to the invention. The unit is only shown schematically here, for example the detailed line paths contained, the valve circuits and the other instrumentation are absent. In addition, for a better overview, the blocks shown in each case represent the functional zones and not individual separating columns. The symbol FI represents a continuous flow measurement, FIC and LIC represent continuous flow or level regulations including the measuring and control devices needed for this. Q, provided with different indices, in each case represents a mass flow which occurs in a certain position of the chromatography unit.

The circulation stream, as can be seen in FIG. 1, is interrupted/separated by an intermediate container. In addition to robust mass flow regulation, this additionally allows a discharge of fractions containing potential impurities in the running operation, which can be determined by suitable online analysis such as, for example, UV, NIR, RI or US (in FIG. 1 marked as QIS). The pump arranged in a fixed manner behind the intermediate container here conveys the eluent stream with constant flow directly to the first separating column of the SMB chromatography unit, mainly independently of whether the eluent is discharged after flowing through the unit or fed back in a closed circulation via the intermediate container.

In order that a circulation flow pump is saved and an eluent pump having constant flow is used, it is not necessary to compensate the separating capacity-disrupting holdup volume of the circulation flow pump by additional measures, such as, for example, asynchronous timing, alteration of the column length or flow adjustment (see prior art above). The further development of the asynchronous timing in one zone to the asynchronous timing of a number of or all zones is thus also superfluous, since the separating capacity in the process according to the invention can also already be achieved directly by the holdup-optimized circuit of the chromatography unit according to the invention.

Likewise, by the described discharge of contaminated eluent fractions in the circulation flow, laborious stoppage or even startup and shutdown of the unit are avoided. In addition to the more robust control, this furthermore increases the economy of the process due to the described invention.

The more robust separating process of multicolumn chromatography in countercurrent operation according to the invention moreover allows a more efficient integration into the preparation process of chemicals and pharmaceuticals. Thus a reactor can be connected upstream and the starting material connected directly as a feed to the multicolumn chromatography unit. Likewise, recovery of nontarget fractions after further rearrangements or reactions, such as, for example, re-racemization by means of pH or temperature shift, are more efficiently possible in the feed mixture or the reactor.

A further point is that both the downstream connected solvent workup and product workup by means of evaporation, drying and/or crystallization steps can be carried out more efficiently, since by means of the described invention the throughput is higher, the product dilution lower and the operating flows more constant; technically a working point can be chosen which is nearer to the theoretical optimum.

In a particularly preferred embodiment, a novel modular valve system (MVS), which itself is also a subject of this invention, additionally replaces the known one-way or multiway fittings and is characterized here by its versatility. The process paths to be switched can be realized by incorporation of the valve heads in a single distributor body. In addition, process parameters (such as, for example, pressure, temperature or concentrations) can also be determined by means of appropriate adaptations. The MVS is distinguished by its compact manner of construction, the modular expandability, cGMP-relevant features (avoidance of dead volumes, good cleanability) and high ease of maintenance. The valve seats can be replaced in the most simple manner and adjusted to the needs. The compactness makes possible very short circuit times with very high circuit cycles. By means of these significant improvements, the unit availability on the pilot and production scale can be markedly increased. Moreover, it is possible using this invention to operate units nearer to the theoretical optimum which increases the throughput/the productivity of the entire unit.

From WO 03/052308, a valve is already known which is of modular construction and can be actuated pneumatically. A characteristic of this valve is an extremely small closing stroke of the valve spindle. On account of the construction of this valve, however, only a monodirectional flow of the valve is possible, whereby this valve is unusable for the use according to the invention.

In order to facilitate the simplification of the SMB process to the process according to the invention and to make possible an improved and thus preferred embodiment, it was necessary to develop a valve which has extremely low closing times in the OPEN/CLOSED position, performs a very large number of switching cycles without showing wear phenomena, exhibits very low product-side dead spaces, has small structural dimensions and can be flowed through with product from both sides, so that in addition to the valve function in basic use operational cleaning processes by means of reversed flow directions and CIP (Cleaning in Place) or SIP (Sterilization in Place) can also be accomplished simply. Moreover, high process requirements with respect to pressure and temperature must not restrict the functionality of the valve. In particular in the case of a circuit of a number of valves in a very small space, it is absolutely necessary to produce compact valves having few components in a modular design, which make a very low holdup and thus sharp separating capacities possible in switching processes. In spite of a small switching path, the ideal valve should have a position indicator, by means of which the user can identify the actual valve position at any time. The automatic or mechanical switching of the valve to a specified process-side safety position in the case of control energy outage should in the best case also still be made possible. No valve known from the prior art can cope with these requirements in a completely satisfactory manner.

Surprisingly, however, it is possible to build an MVS which particularly fulfills the above-mentioned requirements. This MVS according to the invention consists of a master board (10), on which at least one valve according to the invention is installed. The valve according to the invention consists of a valve housing (20) and a control housing (30), the control housing having an interior pneumatic space, which is divided into a lower control space (33) and an upper control space (34) by a piston (31) having a seal (32). The lower control space is separated from the valve housing by a closing plate (35) and additional seals (36). On the piston is located an extended valve spindle (37), which runs through the valve housing up to the seal seat (11) in the area of the master board. The valve housing and the control housing are fixed to one another using a centering plate (21) with seals (22). The valve housing is positioned relative to the master board using a second fixing, the seal seat (11) using associated seals (12), such that a channel connection by means of the seal seat in the product space of the valve housing is created by means of a supply channel (13) having a lateral transverse channel (14) in the master board. From the product space, in turn, a discharge channel (15) for product discharge is available, by which with the supply channel together a flow channel is formed. The valve spindle is bilaterally extended to the piston such that on the one hand the valve spindle reaches through the upper control space to outside the control housing and on the other hand the valve spindle is extended through the valve housing into the seal seat, the valve spindle having a sealing contour to the valve seat and completely closing in the closed position the extended transverse channel and preventing the product flow. The seal seat is positioned with its seals half in the master board and half in the valve housing, such that all valve parts are centred and positioned during installation.

In addition, a characterizing feature of the MVS is that a number of valves are arranged in a space-saving manner, such that a common master board having a common central supply channel can admit at least two valve seats having an identical number of transverse channels and forms particularly low dead-space block valves which make possible the necessary sharp substance separation in process chromatography by means of appropriate control.

This type of valve according to the invention is characterized in a further particular embodiment in that the pressurized control space and the pressurized product space are separated by a pressure-less space and as a result leakage monitoring is made possible.

The valve according to the invention has a particular seal contour pairing between the lower, extended valve spindle and the seal seat, characterized in that different contour pairings and material pairings combine in order to form concentric seal contours, which safely prevent product flow in the closed position of the valve, a round to conical contour pairing preferably being used.

Further preferred contours for the valve spindle and seal seat are concave and or convex designs of spherical and conical contours, but combination with straight surfaces is also possible.

In one particular embodiment, the sealing valve spindle is designed such that the sealing ends of the valve spindle are hollowed out in order to employ a complete sphere, to bond both parts, and to obtain an extremely smooth surface contour for the sealing function. In a particularly preferred embodiment of the valve spindle having a sphere, the sphere extends the valve spindle around the sphere radius and very particularly preferably the sphere extends the spindle around the half radius.

Various embodiments of the valves on master boards offer particular advantages for the acceptance of at least two of the valve sets according to the invention, the master board being designed in the form of a square or hexagonal rod and particularly preferably in spatial shape up to a dodecahedron, the number of valves situated on the master board being reduced by one to two based on all surfaces of the master board. By means of the common master board, it is possible to position two, three, four and more valves in a very small space, one to two areas having to remain free on the master board for the central supply and discharge of the product.

The extension of the valve spindle by the control housing makes possible the external application of a position detector, which signals the current valve position.

Likewise, a subject of this application is therefore also block valves which consist of a master board on which at least two valve housings each having a control housing and in each case associated internal components, and a position indicator is attached to each control housing.

The position indicator makes possible to the operator a visual indication of the actual valve position, which position indicator is based on an electrical and or electronic and or mechanical signal generation, such that an inexpensive visual position indicator is producible.

In a preferred embodiment of the valve according to the invention, the valve seat is situated completely in the master board.

The closing stroke of the valve spindle is preferably less than 5 mm, particularly preferably less than 3 mm and very particularly preferably less than 1 mm.

All metallic and nonmetallic materials can be used for the preparation of the valve.

In a further embodiment, the valve spindle contours seals the valve in the seal seat and the diameter course of the concentric seal area of the two contours is greater than the hydraulic diameter of the transverse channel, preferably, the seal range is 1.1 to 1.3 times and particularly preferably the seal area lies on a diameter in the seal seat of 1.4 to 1.6 times the hydraulic diameter of the transverse channel.

The valves according to the invention are particularly suitable for guaranteeing a reciprocal sharply separating product flow in process chromatography units. Block valves of small construction with a central master board are particularly suitable for use in process chromatography units.

In process chromatography units according to the invention which essentially consist of a number of columns connected in series, the columns arbitrarily having to be capable of being cut off mutually or to one another, valves are continuously pressurized by means of the product supply and the product discharge line, in addition the valves are alternatively switched at short time intervals in order, for example in the case of different fractions (product specifications) to make possible a rapid and sharp separation. Since the products are generally expensive, on account of the low closing stroke between the OPEN and CLOSED position the valve according to the invention increases the efficiency of the entire process chromatography unit. The high valve functionality of the valves, which is achieved in the form of a high leak tightness with, at the same time, a high number of switching cycles, is particularly important. Use in batch chromatography units is therefore also possible.

Figure 7:
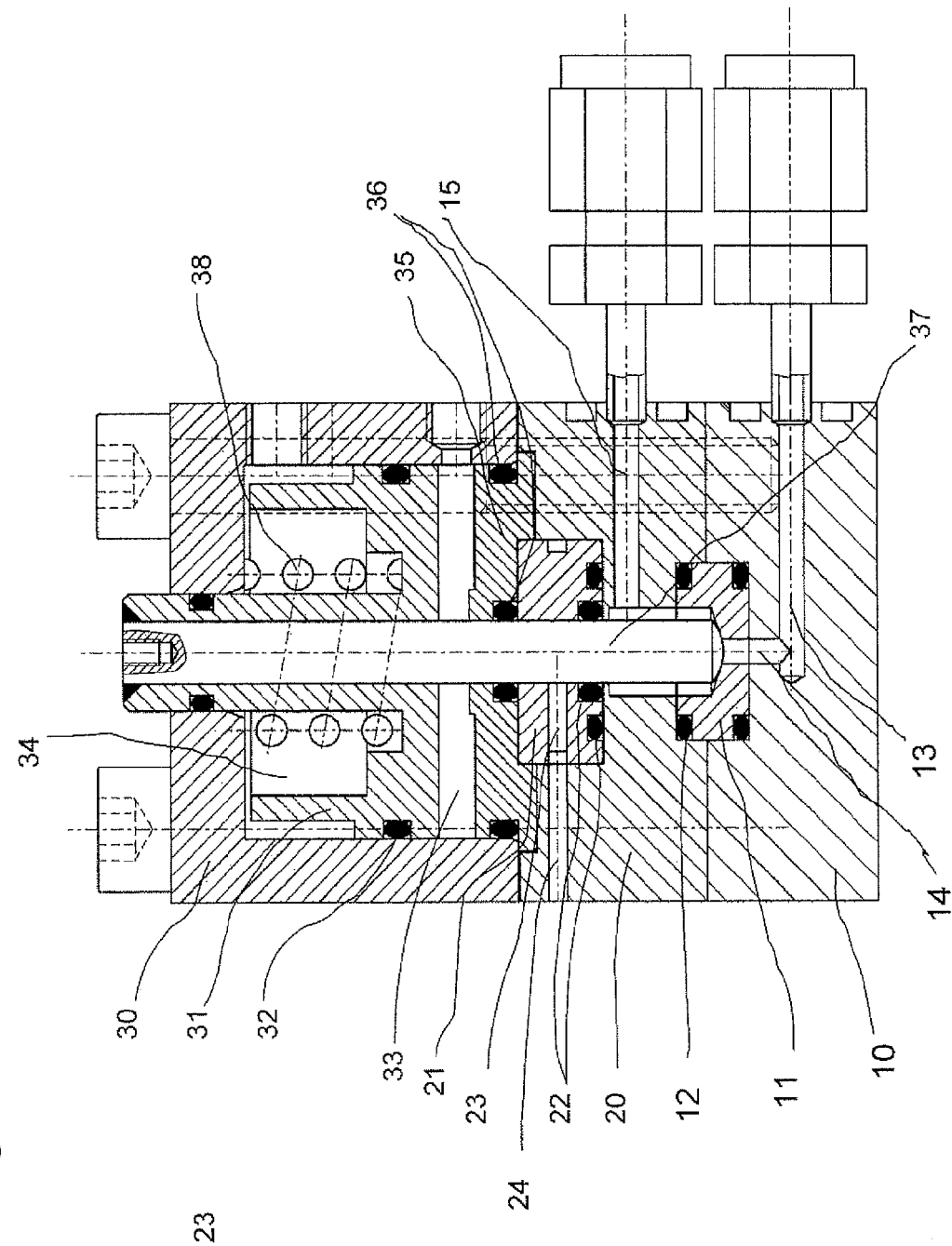
FIG. 7 shows the inventive valve with individual components.

In FIG. 6, four inventive valves (1, 2, 3, 4), according to FIG. 7, installed on a common master board, are shown.

In FIG. 7, all individual valve parts are shown on a common master board (10). It can be seen in FIG. 7 that the master board (10) has a central supply channel (11) for the product and from the supply channel four transverse channels (14) branch off to the valves adapted to the master board. At least two further valves can be installed on the master board, in which a further valve housing (20) and control housing (30) having appropriate fixing elements (e.g. screws) are detachably connected to the master board. The valve housing is centered on the master board by means of the seal seat (11) and the centering of the control housing is carried out using a centering plate (21), which engages in the closing plate (35). In the control housing is a piston (31) having a firmly connected bilaterally extended valve spindle (37), in order to form an upper and lower control space (33, 34) in the control housing. The extended valve spindle extends on the one side up to the seal seat and on the other side to outside the control housing, in order, if appropriate, to be able to admit a position detector outside the valve. The inner parts of the valve are provided with elastic seals, such that a product flowing through is specifically conducted by the valve, cannot escape outward, product space and control space are separate from one another and leakage or failure of a seal is recognized. In addition, the seals employed serve to seal individual valve components in their planes. The seal (32) on the piston separates the upper and lower control space. The two seals (36) separate the lower control space from the pressureless valve space, the inner seal sealing to the valve spindle and the outer seal sealing to the control housing. The centering plate (21) likewise has two seal (22) in one plane, such that one seals the product space to the valve spindle and the other prevents a bypass flow. The centering plate has a transverse drilling (23), which is extended outwards through the transverse drilling of the valve housing (24), such that a pressureless intermediate space is formed between the product space and control space. The transverse drillings signal a leakage or a failure of the product-side seals.

The flowing through of the valve with product takes place by means of the central supply channel, the transverse channel (14) and the seal seat, such that the end of the valve spindle contour is flowed around and the product can flow through the discharge channel (15) from the valve. The product flowing through is prevented if, for example, an employed pressure spring (38) in the upper control space presses the piston with valve spindle into the contour of the seal seat. The valve opens if, for example, in the lower control space the attached compressed air builds up pressure and the compressive force generated is greater than the spring force in the upper control space, such that the piston is raised, the valve spindle separates from the seal seat, and a liquid or gaseous substance can pass.

In FIG. 6, three further positions of the master board are occupied by valves in order to form a four-block valve.

Figure 8:
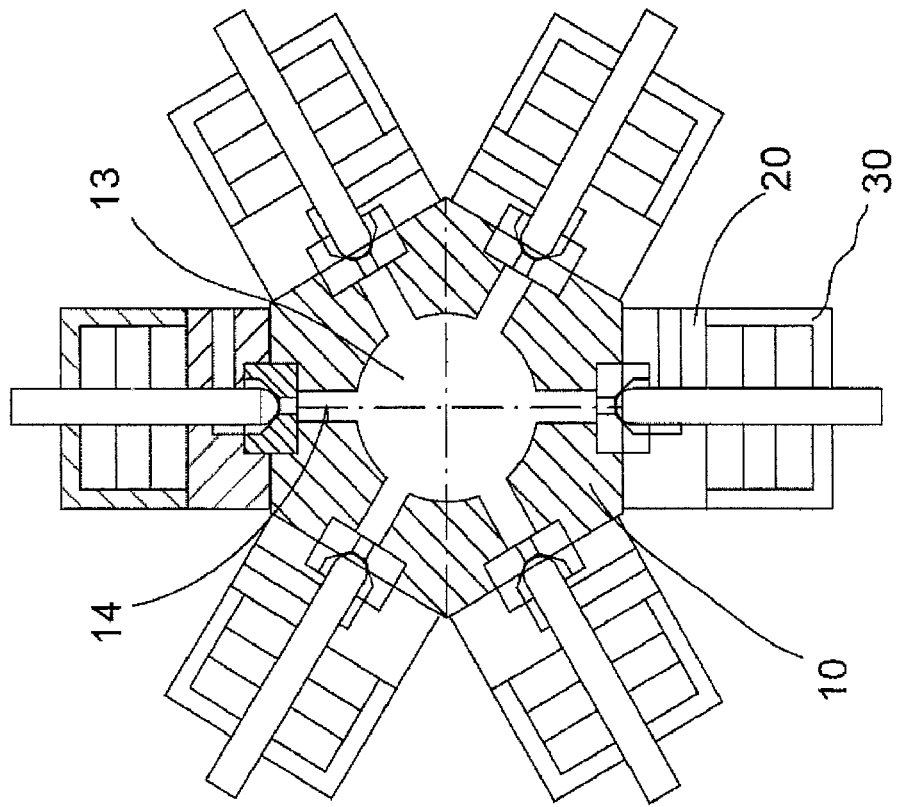
FIG. 8 shows, by way of example, a hexagonal master board or rod.

FIG. 8 shows the cross-section of a hexagonal rod or hexagonal master board (10), the central supply channel (13) and the transverse channels (14) being incorporated in the hexagonal master board, and a receiving drilling of the seal seats being incorporated on each outer surface. FIG. 8 shows clearly that six valves with the valve housing (20) and control housing (30) can be positioned in a narrow space and in the case of a hexagonal rod even a multiple of six valves one after the other is handleable in the narrowest space. It is not urgently necessary here, however, to equip each valve position.

Figure 9:
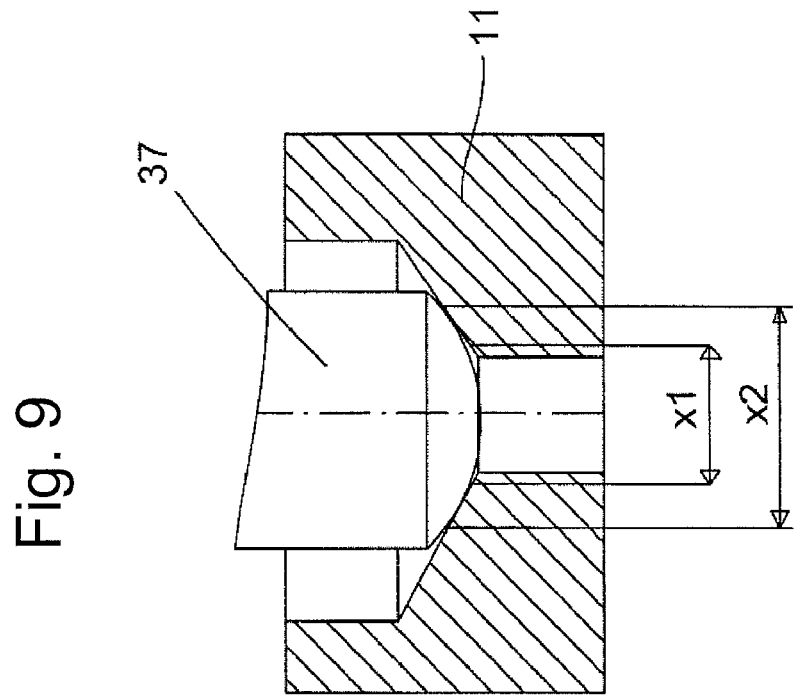
FIG. 9 shows the preferred concentric seal area.

In FIG. 9, the special seal contours of the valve spindle (37) and of the seal seat (11) are shown. It can be seen that the preferred seal area (X2–X1) is greater than the hydraulic cross-section of the transverse channel. This has the advantage that with a high number of switching cycles at high differential pressures the sealing contours are not deformed.

Figure 10:
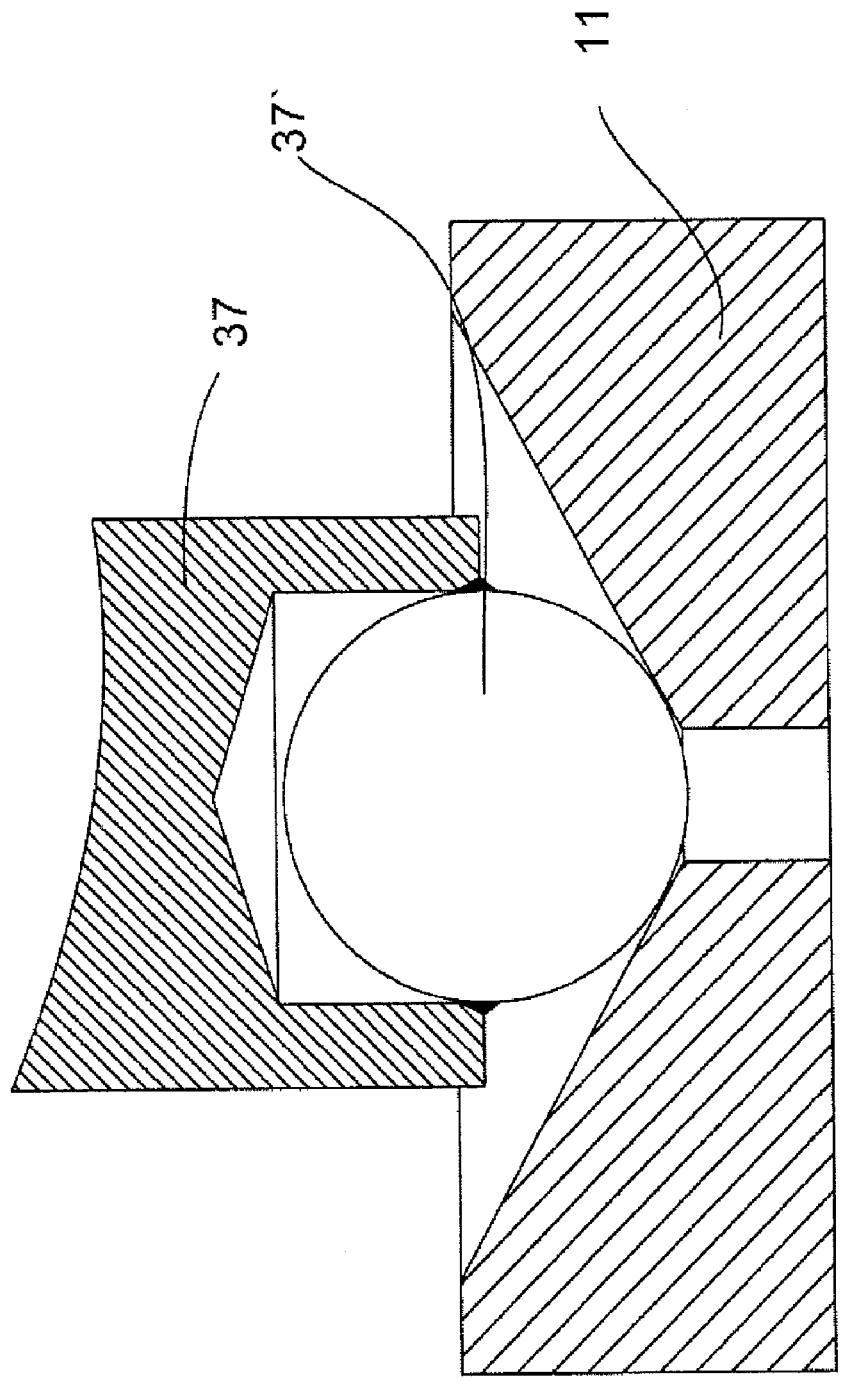
FIG. 10 shows a particular design of the sealing valve spindle contour.

In FIG. 10, a special form of the sealing valve spindle contour (37) is shown. Here, the production of a very smooth sealing surface is carried out, by way of example, by the application of a sphere (37'). The sphere projects here partially into the cross-section of the valve spindle and a part of the sphere is available elevated as a sealing contour.

An embodiment of the process according to the invention is likewise preferred in which a certain mass flow control is employed, which surprisingly leads to a further performance increase and is likewise a subject of the present invention.

In the SMB unit according to the invention, the operating point is specified by means of the external streams feed $Q_F$, extract $Q_{Ex}$ and raffinate $Q_{Raf}$ and the internal eluent stream $Q_I$ and timing period $\tau$.

A mass flow control has now surprisingly been found (see FIG. 1), in which the mass flows $Q_F$, $Q_{Ex}$, $Q_{Raf}$ and $Q_I$ are continuously measured and directly regulated by means of the speed of rotation of the corresponding pumps (4-pump procedure). Alternatively, the adjustment of the product streams $Q_{Ex}$ and $Q_{Raf}$ by means of suitable regulating valves instead of discharge pumps is possible (2-pump procedure). The adherence of the total mass balance, and thus the correct adjustment of the desorbent stream $Q_D$ as the remaining external stream, is also achieved by the filling level regulation in the eluent receiver. This filling level regulation compensates the deviations from the nominal mass balance inevitably caused by disturbances and/or measuring errors and determines, together with the switching on of the nominal desorbent amount resulting from the balances, $$Q_D^0 = Q_{Ex} + Q_{Raf} - Q_F + Q_{Dest} \quad (2)$$

the flow of freshly added desorbent (eluent):

$$Q_D = Q_D^0 + \Delta Q_D^{LIC}. \quad (3)$$

This value is then adjusted by means of the flow regulation of the desorbent amount and monitored by means of continuous flow measurement.

In a very particularly preferred embodiment, a continuous online analysis measurement QIS is introduced into the recycle line after zone IV (FIG. 1). In the case of contamination of the solvent stream fed back (e.g. breakthrough of product from zone IV), this triggers a corresponding valve circuit, such that the contaminated solvent stream is discharged and is not fed back into the eluent receiver.

The additional flow measurement in the recycle stream serves, in the case of quality-related discharge of the recycle stream, for the determination of $Q_{Dest}$, in operation as intended, by the utilization of the redundancy achieved with the measurement of the flow $Q_{Dest}$ in the mass flow measurements and balances, a measurement data validation (data reconciliation) is performed for all mass flows and thus the accuracy of the mass flow regulation is additionally increased.

The mass flow regulation according to the invention makes possible—in particular by dispensing with a pressure regulation for the conclusion of the mass balance—a more accurate and more robust adjustment of the mass flows for the confirmation of the separating capacity of the unit.

The very particularly preferred embodiment according to the invention of a combination of the unit and regulation concept makes possible both operation with a closed and with an open circulation. In the case of open circulation, by means of the online analysis measurement in the recycle line, a possible impurity can be directly discharged. In the conventional circulation operation, discharge of impurities is only possible by means of the product streams and thus associated with a loss of yield.

The redundancy in the mass flow measurements provided according to the invention and the measuring error balance for the flow measurements based thereon additionally increases the accuracy of the mass flow regulation and thus confirms the fulfillment of the separation task.

Using the unit and regulation concept according to the invention, variable dead volumes and the process disruptions associated therewith are avoided. Special countermeasures such as, for example, the asynchronous switching of the valves are thus no longer necessary.

The following examples are intended to illustrate the present invention without, however, restricting it:

FIG. 5 shows the integration of the multicolumn chromatography process in an overall process for the preparation of chemical and pharmaceutical substances as exemplified by racemic substances. There is the possibility directly, without intermediate storage after the reaction, leading the reaction mixture continuously into the chromatography unit. Furthermore, the direct workup and the recycling of the solvent from the product streams extract and raffinate into the eluent receiver is possible. The quality of the eluent must be measured and adjusted before use again in the chromatography unit. For this, depending on the eluent composition required, a number of offline methods (such as, for example, GC and HPLC) and online methods (such as, for example, ultrasound, capacitative, NIR) are available. From a feed container, in a further container the feed mixture of solid or fluid consistency is introduced in the specified eluent composition. Extract and raffinate are supplied from the chromatography unit to evaporators and the evaporated solvent is recycled into the eluent container. Fresh solvent is metered in from various eluent receiver containers, depending on the number of solvents involved in the eluent mixture, until the required eluent specification is achieved in the eluent supply to the chromatography unit. The concentrated product after evaporating is stored in containers and generally crystallized, filtered and dried in the further product workup. The byproduct—in the example case the "wrong" enantiomer—is usually re-racemized for economic reasons (often, for example, by pH or temperature change) and after quality control added to the feed mixture derived from the original reaction stage.

The invention claimed is:

1. A process for the separation of a substance mixture with the aid of a countercurrent chromatography process, in which a substance mixture to be separated and the eluent are continuously supplied to a column circuit consisting of more than one chromatography columns packed with an adsorbent and connected in series and in other positions of the column circuit an extract stream comprising at least one separated component, and a raffinate stream comprising at least one other component are continuously removed and in which a relative movement between a liquid, mobile phase consisting of the substance mixture and the eluent and the adsorbent in solid phase is produced by sequential opening of liquid addition and removal positions along the columns, characterized in that only one eluent supply pump and an eluent compensation container within the circulation, but no circulation pump is employed in the circulation.

2. The process as claimed in claim 1, characterized in that at most 4 pumps are employed in the chromatography circulation.

3. The process as claimed in claim 1, characterized in that at least one discharge pump, extract or raffinate discharge, is replaced by a control valve.

4. The process as claimed in claim 1, characterized in that an automatic discharge of contaminated eluent in the circulation is made possible by means of an online detection and a control valve.

5. The process as claimed in claim 1, characterized in that the accuracy of the mass flow control is increased by measurement of the recyclate stream and the redundancy thus achieved by means of a measured data balance.

6. The process as claimed in claim 1, characterized in that in the mass flow regulation the adherence to the total mass balance is achieved by means of a filling level regulation in the eluent compensation container.

7. A process for the preparation of a product, characterized in that the product mixture derived from the reaction is fed directly into a process as claimed in claim 1 and then worked up.

* * * * *